(12) United States Patent
Blezek et al.

(10) Patent No.: US 9,042,611 B2
(45) Date of Patent: May 26, 2015

(54) AUTOMATED VASCULAR REGION SEPARATION IN MEDICAL IMAGING

(75) Inventors: Daniel J. Blezek, Mantorville, MN (US); Bradley J. Erickson, Rochester, MN (US); Peter J. Schommer, Rochester, MN (US); David R. Limpert, Rochester, MN (US); Nelson Ramirez, Rochester, MN (US)

(73) Assignees: Mayo Foundation for Medical Education and Research, Rochester, MN (US); International Business Machines Corporation, Armonk, NY (US)

( * ) Notice: Subject to any disclaimer, the term of this patent is extended or adjusted under 35 U.S.C. 154(b) by 352 days.

(21) Appl. No.: 13/574,717

(22) PCT Filed: Jun. 30, 2010
(Under 37 CFR 1.47)

(86) PCT No.: PCT/US2010/040593
§ 371 (c)(1),
(2), (4) Date: Dec. 20, 2012

(87) PCT Pub. No.: WO2011/093921
PCT Pub. Date: Aug. 4, 2011

(65) Prior Publication Data
US 2013/0202170 A1    Aug. 8, 2013

Related U.S. Application Data

(60) Provisional application No. 61/299,527, filed on Jan. 29, 2010.

(51) Int. Cl.
*G06K 9/00* (2006.01)
*G06T 7/00* (2006.01)

(52) U.S. Cl.
CPC .......... *G06K 9/00201* (2013.01); *G06T 7/0093* (2013.01); *G06T 2207/10072* (2013.01); *G06T 2207/20081* (2013.01); *G06T 2207/20128* (2013.01); *G06T 2207/30101* (2013.01)

(58) Field of Classification Search
CPC ................. G06K 9/00201; G06T 2207/10072; G06T 2207/20081; G06T 2207/20128; G06T 2207/30101; G06T 7/0093
USPC .................................. 382/128, 131, 132, 154
See application file for complete search history.

(56) References Cited

U.S. PATENT DOCUMENTS 5,273,040 A * 12/1993 Apicella et al. ................ 600/410
5,671,265 A *  9/1997 Andress ..................... 378/98.11
(Continued)

OTHER PUBLICATIONS

Mattes et al., "PET-CT image registration in the chest using free-form deformations," TMI, vol. 22, pp. 120-128, Jan. 2003.
(Continued)

*Primary Examiner* — Tom Y Lu
(74) *Attorney, Agent, or Firm* — Shumaker & Sieffert, P.A.

(57) ABSTRACT

A system and/or method automatically identifies one or more vascular regions in a medical image or set of medical images. For example, the system/method may automatically identify vascular structures as belonging to the left carotid, right carotid, and/or basilar vascular regions in the head. The system/method takes as input the medical image(s) and automatically identifies one or more vascular regions. The system/method may also automatically generate MIP renderings of the identified region or regions.

11 Claims, 13 Drawing Sheets

(56) References Cited

U.S. PATENT DOCUMENTS

| | | | |
|---|---|---|---|
| 6,845,260 B2 | 1/2005 | Liu et al. | |
| 7,020,314 B1* | 3/2006 | Suri et al. | 382/130 |
| 7,024,027 B1 | 4/2006 | Suri et al. | |
| 8,023,711 B2* | 9/2011 | Scheuering et al. | 382/131 |
| 8,811,724 B2* | 8/2014 | Nielsen et al. | 382/159 |
| 2007/0008317 A1* | 1/2007 | Lundstrom | 345/424 |
| 2007/0019846 A1 | 1/2007 | Bullitt et al. | |
| 2007/0116332 A1 | 5/2007 | Cai et al. | |
| 2007/0140541 A1 | 6/2007 | Bae et al. | |
| 2010/0054563 A1* | 3/2010 | Mendonca et al. | 382/131 |

OTHER PUBLICATIONS

Lee et al., "Building Skeleton Models via 3-D Medial Surface/Axis Thinning Algorithms," CVGIP: Graphical Models and Image Processing, v56, n6, p. 462-478, Nov. 1994.

Uchiyama et al., "Automated Classification of Cerebral Arteries in MRA Images and Its Application to Maximum Intensity Projection," Engineering in Medicine and Biology Society 2006, 28th Annual International Conference of the IEEE, Aug. 30-Sep. 3, 2006, pp. 4865-4868.

Yang et al., "Computer-Aided Detection (CAD) of Intracranial Aneurysms in MR Angiography," SIIM 2009 Annual Meeting, Jun. 4, 2009, Charlotte, NC, 3 pp.

Zhou et al., "Learning with Local and Global Consistency," Advances in Neural Information Processing Systems 16, MIT Press, 2004, pp. 321-328.

Akinyemi et al., "Automatic Labelling of Coronary Arteries," 17th European Signal Processing Conference, Glasgow, Scotland, Aug. 24-28, 2009, pp. 1562-1566.

Shattuck et al., "Construction of a 3D probabilistic atlas of human cortical structures," NeuroImage 39 (2008):1064-1080.

Fischl et al., "Whole Brain Segmentation: Neurotechnique Automated Labeling of Neuroanatomical Sturctures in the Human Brain," Neuron, vol. 33, pp. 341-355, Jan. 31, 2002.

Passat et al., "Cerebral Vascular Atlas Generation for Anatomical Knowledge Modeling and Segmentation Purpose," 2005 IEEE Computer Society Conference on Computer Vision and Pattern Recognition, vol. 2, Jun. 20, 2005, pp. 331-337.

Chalopin et al., "Automatic Labeling of the Coronary Tree Using a Three Dimensional Reference Prior Model," Computers in Cardiology, vol. 25, 1998, pp. 761-764.

Ezquerra et al., "Model-Guided Labeling of Coronary Structure," IEEE Transactions on Medical Imaging, vol. 17, No. 3, Jun. 1, 1998, pp. 429-441.

Lesage et al., "A review of 3D vessel lumen segmentation techniques: Models, features, and extraction schemes," Medical Image Analysis 13 (2009): 819-845.

Stefancik et al., "Highly automated segmentation of arterial and venous trees from three-dimensional magnetic resonance angiography (MRA)," The International Journal of Cardiovascular Imaging 17: 37-47, 2001.

International Search Report and Written Opinion of international application No. PCT/US2010/040593, dated Nov. 2, 2010, 25 pp.

International Preliminary Report on Patentability from international application No. PCT/US2010/040593, dated Aug. 9, 2012, 15 pp.

Ibanez et al., The ITK Software Guide, Second Edition, Updated for ITK version 2.4, Nov. 21, 2005, 836 pp.

* cited by examiner

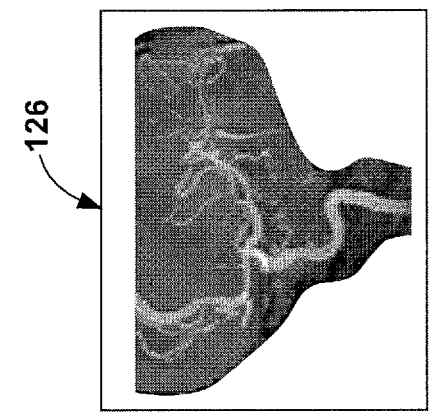
Fig. 11B
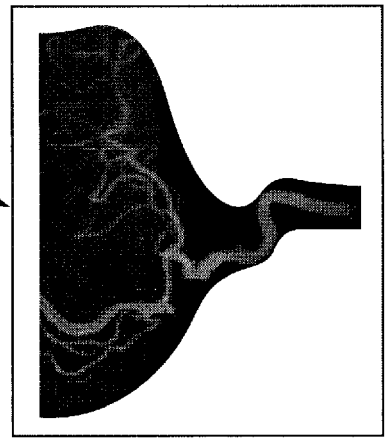
Fig. 12B
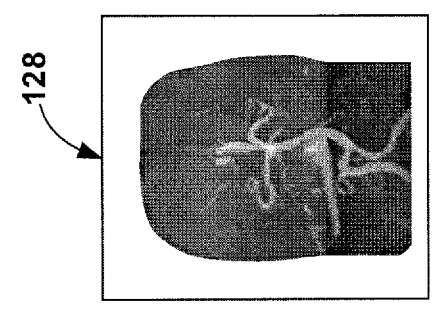
Fig. 11C
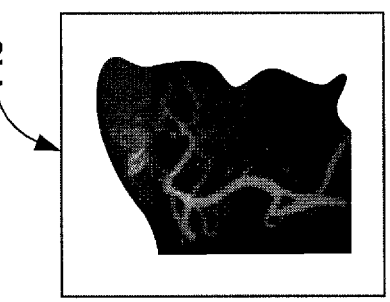
Fig. 12C
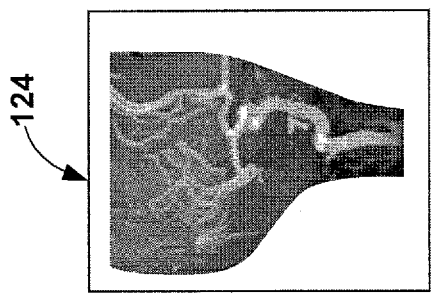
Fig. 11A
Fig. 12A

AUTOMATED VASCULAR REGION SEPARATION IN MEDICAL IMAGING

CROSS REFERENCE TO RELATED APPLICATIONS

This application claims the benefit of U.S. Provisional Application No. 61/299,527, filed Jan. 29, 2010, which is incorporated herein by reference in its entirety.

TECHNICAL FIELD

The disclosure relates generally to medical imaging of blood vessels.

BACKGROUND

Neuroradiologists' ability to successfully interpret magnetic resonance angiography (MRA) images is enhanced when projection images called maximum intensity projection (MIP) renderings are independently generated for the three main vascular structures in the head. Currently, this process is performed manually by the MR technician immediately following the acquisition of an MR angiography series. The technician uses tools provided on the scanner to manually trace out the left carotid arterial tree, the right carotid arterial tree and the basilar/posterior arterial tree. Though straight forward, this process requires approximately 10-20 minutes of technician's time. As radiology departments continue to seek methods of work flow improvement, even 20 minutes of technician's time become valuable.

SUMMARY

The disclosure relates generally to a system and/or method that automatically identifies one or more vascular regions in a medical image or set of medical images. For example, the system/method may automatically identify vascular regions such as left, right and/or basilar vascular regions in the head. The system/method takes as input the medical image(s) and identifies one or more vascular regions. The system/method may also produce MIP renderings of the identified region or regions.

In one example, the disclosure is directed to a method comprising determining a probability for each voxel in a patient-specific image data set that the voxel belongs to one or more vascular regions of interest, segmenting patient-specific vasculature in the patient-specific image to generate a set of nodes and edges representative of the patient-specific vasculature, classifying each node and edge based on one or more statistics associated with each node and edge, and determining to which of the one or more vascular regions of interest each voxel in the patient-specific image data set belongs based on the probability and the classifications. The method may further include determining whether each voxel in the patient-specific image data set belongs to a left carotid vascular region, a right carotid vascular region or a basilar vascular region. The method may also include automatically generating a MIP rendering of the vascular region of interest based on the association. The method may also include displaying the MIP rendering on a user interface.

In another example, the disclosure is directed to a method comprising receiving a plurality of manually generated maximum intensity projection (MIP) renderings of a vascular region, each corresponding to one of a plurality of image data sets obtained from subjects in a sample population, generating an anatomic atlas comprised of an average image data set based on the plurality of image data sets obtained from the subjects in the sample population, projecting each voxel in the anatomic atlas into each of the plurality of manually generated MIP renderings, determining, for each voxel in the anatomic atlas, a probability that the voxel belongs to the vascular region based on the projection, and storing the determined probabilities as a probabilistic atlas for the vascular region indicative of a likelihood that each voxel in a patient-specific image data set belongs to vascular region.

In another example, the disclosure is directed to a system comprising a controller that receives a patient-specific image data set, a probability module, executed by the controller, that determines a probability for each voxel in a patient-specific image data set that the voxel belongs to one or more vascular regions of interest, a segmentation module, executed by the controller, that segments patient-specific vasculature in the patient-specific image to generate a set of nodes and edges representative of the patient-specific vasculature, a classification module, executed by the controller, that classifies each node and edge based on one or more statistics associated with each node and edge, and a vessel location analysis module, executed by the controller, that determines to which of the one or more vascular regions of interest each voxel in the patient-specific image data set belongs based on the probability and the classifications.

The details of one or more examples are set forth in the accompanying drawings and the description below. Other features and advantages will be apparent from the description and drawings, and from the claims.

BRIEF DESCRIPTION OF DRAWINGS

FIGS. 11A-11C show examples of automatically generated MIP renderings of the left carotid, right carotid, and basilar vascular regions, respectively.

FIGS. 12A-12C show examples of manually (technician) generated MIP renderings of the left carotid, right carotid, and basilar vascular regions, respectively.

DETAILED DESCRIPTION

The disclosure relates generally to a vascular region separation system and/or method (referred to generally herein as the "vascular region separation system" or simply "system") that identifies the location of one or more vascular regions in a medical image or set of medical images. The system takes as input a patient-specific medical image(s) and identifies the location of one or more vascular regions within the medical image. For example, the system may automatically identify the location of vascular regions in the head such as the left carotid vascular region, the right carotid vascular region, and/or the basilar/posterior vascular region. The system/method may also produce MIP renderings of the identified region or regions.

Although an example system will be described herein with respect to identification of vascular regions in the head, it shall be understood that the system may also identify the locations of other vascular regions in the body. For example, the techniques described herein may be used to identify other vascular regions in the head. The techniques described herein may also be used to identify vascular regions in other anatomic locations in addition to the head. For example, the location of carotid arteries in the neck, veins in the head and neck or other parts of the body, vessels in the legs, coronary arteries in the heart, or other vascular regions in the body may also be identified.

In some examples, the system "automatically" identifies the location of the one or more vascular regions in the data set, meaning that there is no human intervention. In other examples, the system may acquire human input may be acquired before or during the identification process, and the system is therefore "semi-automatic." It shall be understood that the disclosure is intended to cover both automatic and semi-automatic systems and that the disclosure is not limited in this respect.

Figure 2A:
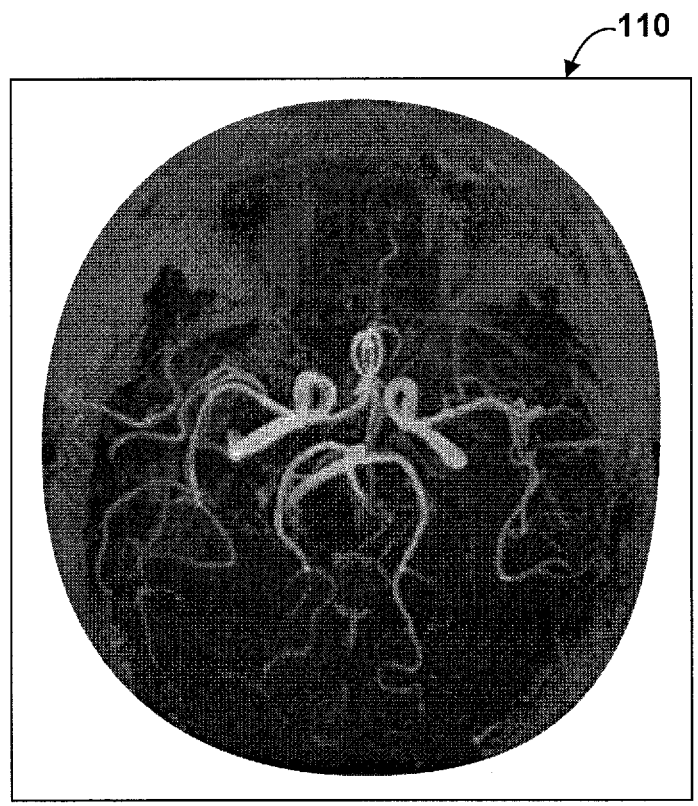
FIG. 2A shows an example MIP rendering of a TOF image from the inferior-superior direction and FIG. 2B shows a MIP of an example anatomic atlas from the same view.

For purposes of the present description, an example implementation in which 3D image data sets are obtained via 3D time-of-flight (TOF) magnetic resonance angiography (MRA) will be described. An example TOF image is show in FIG. 2A. However, it shall be understood that the acquisition could be obtained via direct 3D or multiple 2D images acquired in any way that permits creation of a 3D image set, such as computed tomography (CT), single photon/positron emission computed tomography (SPECT/PET), ultrasound or other medical imaging technique that allows visualization of blood vessels within the body may also be used, and that the disclosure is not limited in this respect.

In general, each slice of a 3D image data set is made up of "pixels," with a potential dynamic range of 16-bits (65,535 grey levels). Medical images are often displayed by compressing and clamping the 16-bit dynamic range into 8-bits, or 256 grey levels where 0 is displayed as black and 255 is displayed as white. Each pixel represents brain tissue which is about, for example, 1 millimeter on each of two sides. The thickness of the slice may be, for example, 3 or 5 millimeters, thus creating a three-dimensional volume element, or "voxel." Pixel intensity generally represents an average from tissue within the voxel.

Figure 1:
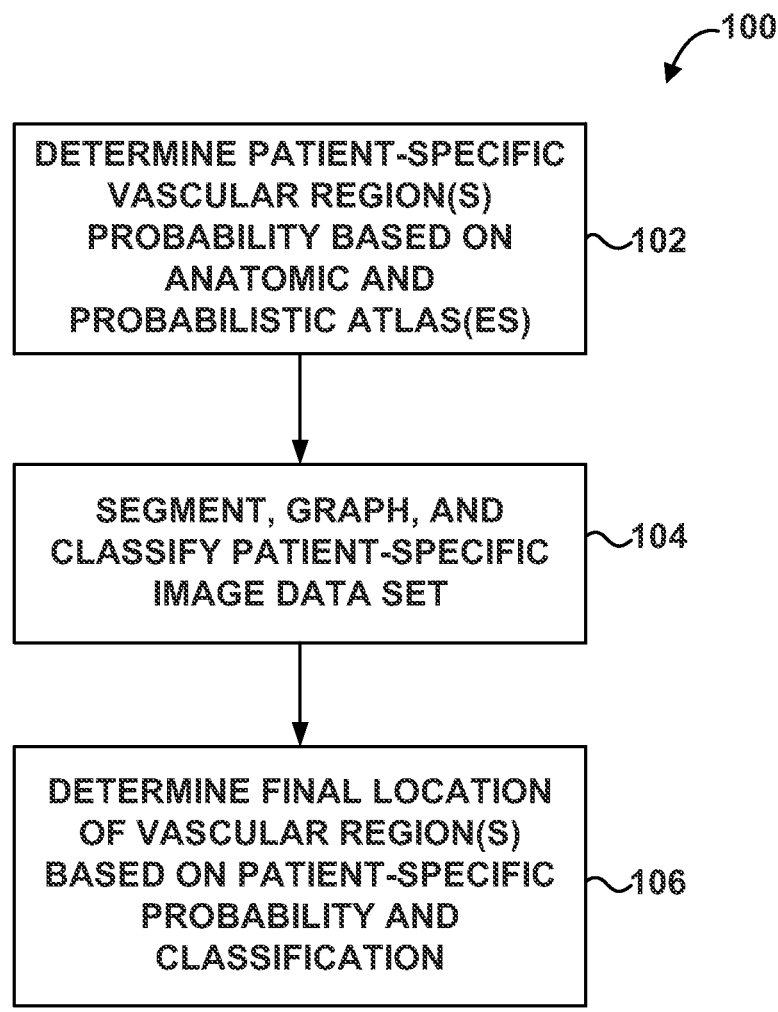
FIG. 1 is a flowchart illustrating an example process by which the vascular region separation system (shown in more detail in FIG. 6) identifies the locations of one or more vascular regions within a medical imaging data set.

FIG. 1 is a flowchart illustrating an example process (100) by which the vascular region separation system (shown in more detail in FIG. 6) identifies the locations of one or more vascular regions within a medical imaging data set. That is, the system automatically identifies vascular structures within a patient-specific image data set as belonging to a particular vascular region. The system thus separates the vascular structures within the patient-specific image data set into the appropriate vascular regions.

Figure 2B:
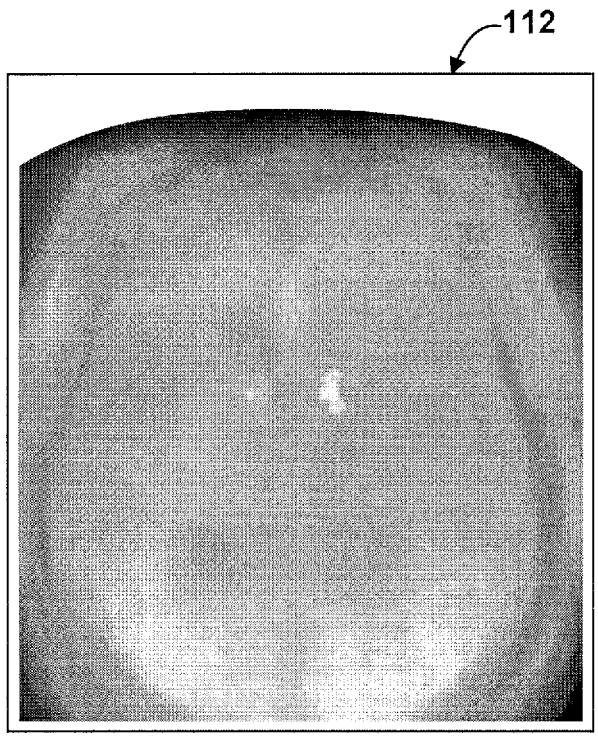
Figure 3A:
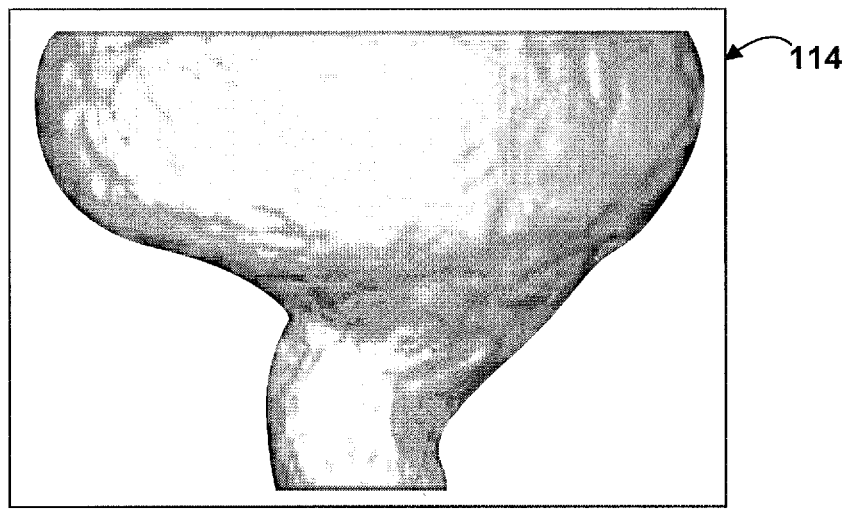
FIGS. 3A-3C show examples of the left carotid, right carotid, and basilar probabilistic atlases, respectively.
Figure 3B:
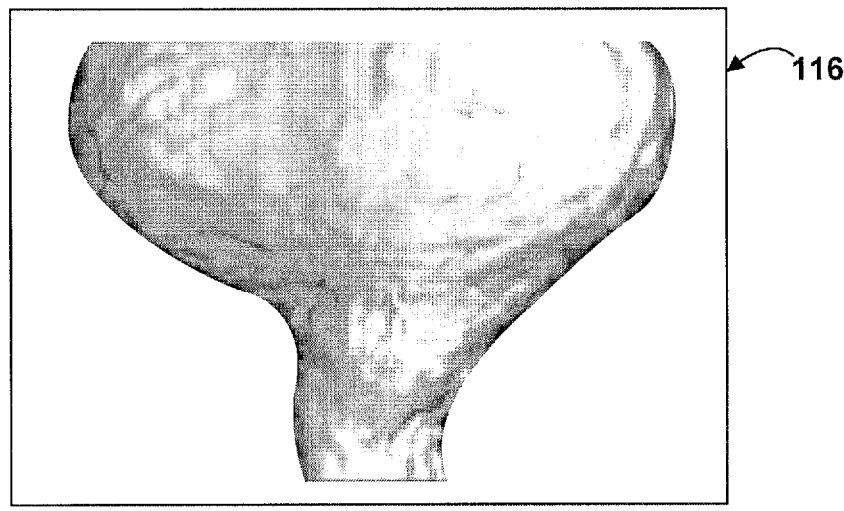
Figure 3C:
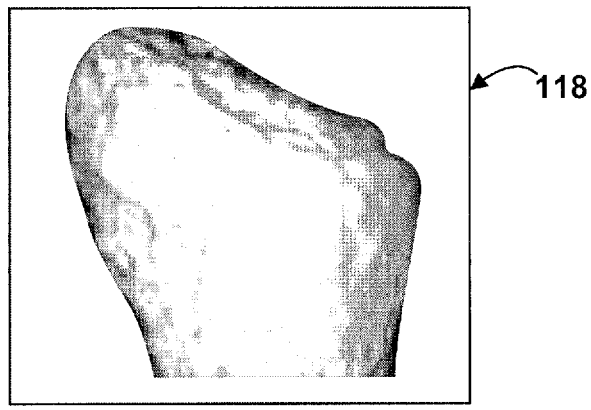

Process (100) includes determining the probability that each voxel in the patient-specific image data set belongs to one or more vascular region(s) (102). The system makes this determination based at least in part on an anatomic atlas and one or more probabilistic atlases. The anatomic atlas may be generated, for example, from a plurality of image data sets taken from subjects in a sample population. As such, the anatomic atlas may typify an average or representative image data set. FIG. 2 shows an example bottom view of a MIP of an example anatomic atlas (average intensity atlas in this example) from 84 TOF data sets. The one or more probabilistic atlases may also be generated based on the plurality of image data sets of the sample population. Each probabilistic atlas corresponds to a different vascular region to be identified and includes the probability that each voxel in an image data set is contained in the corresponding vascular region. FIGS. 3A-3C show examples of the left carotid 112, right carotid 114, and basilar 116 probabilistic atlases from the same 84 TOF data sets. The probabilistic atlases 112, 114 and 116 are shown in this example using gradient shading to somewhat convey the three-dimensionality of the probabilistic atlases. Construction of the anatomic and probabilistic atlases will be described in further detail below.

Referring again to FIG. 1, process (100) also includes segmenting, graphing, and classifying patient-specific vasculature from the patient-specific image data set (104). Once the graph is created, each node and edge in the graph may be classified according to the one or more region(s) it likely belongs to. Once each node and edge in the graph is classified, the probabilistic region locations of the patient are combined with the information from the segmented graph classifications to identify the final location of the one or more vascular regions (106).

Figure 4:
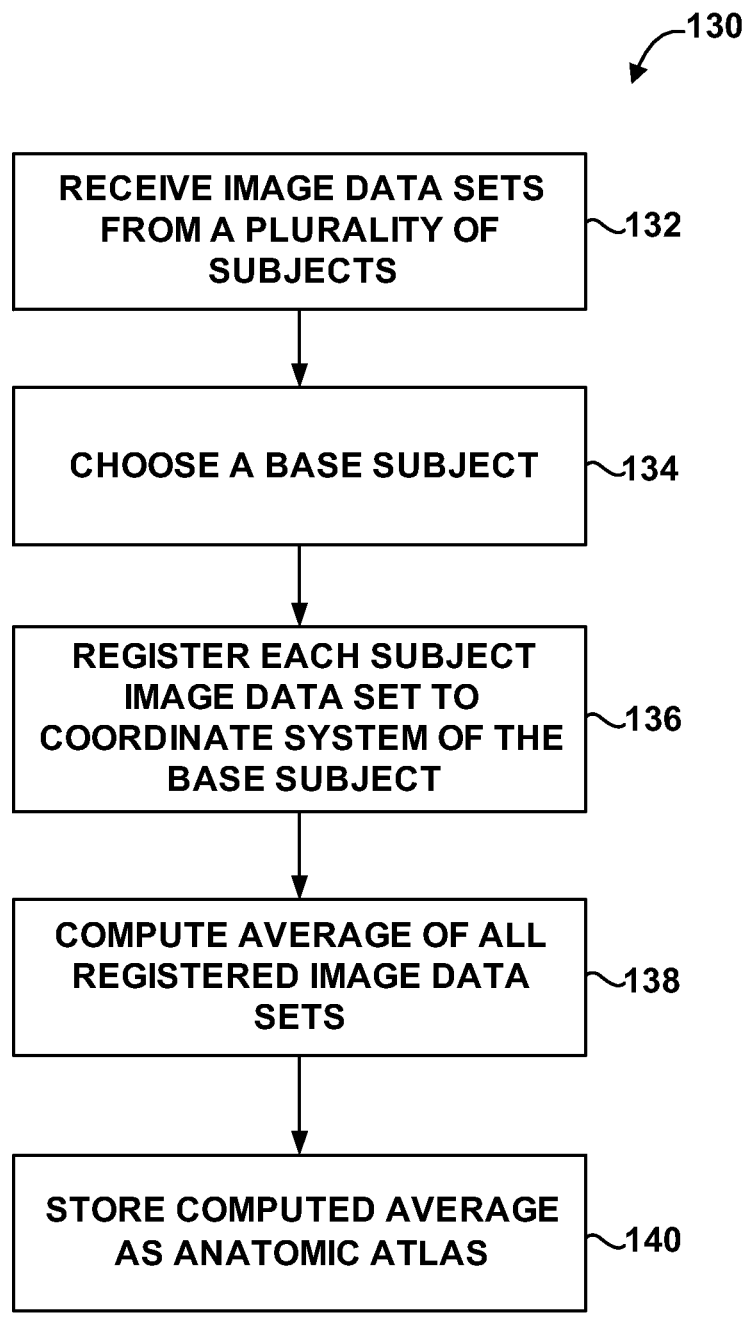
FIG. 4 is a flowchart illustrating an example process by which an anatomic atlas may be constructed.

FIG. 4 is a flowchart illustrating an example process (130) by which an anatomic atlas may be constructed. In this example, the anatomic atlas is constructed from a plurality of image data sets obtained from subjects in a sample population (132). To construct the anatomic atlas, a subject from the population may be chosen at random, or upon some appropriate criteria, to be the "base" of the atlas (134). Each subject image data set is in turn is registered to the image data set of the base subject (or other common coordinate system), e.g., transformed into the coordinate system of the base subject image data set (136). After all subjects from the sample population are registered, the average intensity of all the registered image data sets is computed (138). The computed average of the image data sets is stored as the anatomic atlas (140).

Registration of each subject image data set to that of the base subject or other common coordinate system (136) may be accomplished using any suitable image registration or image alignment methods known in the art. In one example, registration may be accomplished using the Mattes mutual information registration algorithm (described in D. Mattes, D. Haynor, H. Vesselle, T. Lewellen, and W. Eubank, "PET-CT image registration in the chest using free-form deformations," *Transactions on Medical Imaging*, vol. 22, pp. 120-128, January 2003) in a multi-resolution context. In that example, the transformation between the two image data sets being registered is an affine transformation with, for example, 12 degrees of freedom, translation, rotation, scales and shears. The example registration algorithm may be that described in the publication L. Ibanez, W. Schroeder, L. Ng, and J. Cates, *The ITK Software Guide*, Kitware, Inc. ISBN1-930934-15-7, http://www.itk.org/ItkSoftwareGuide.pdf, second edition, 2005). However, it shall be understood that other registration methods may also be used, and that the disclosure is not limited in this respect.

Figure 5:
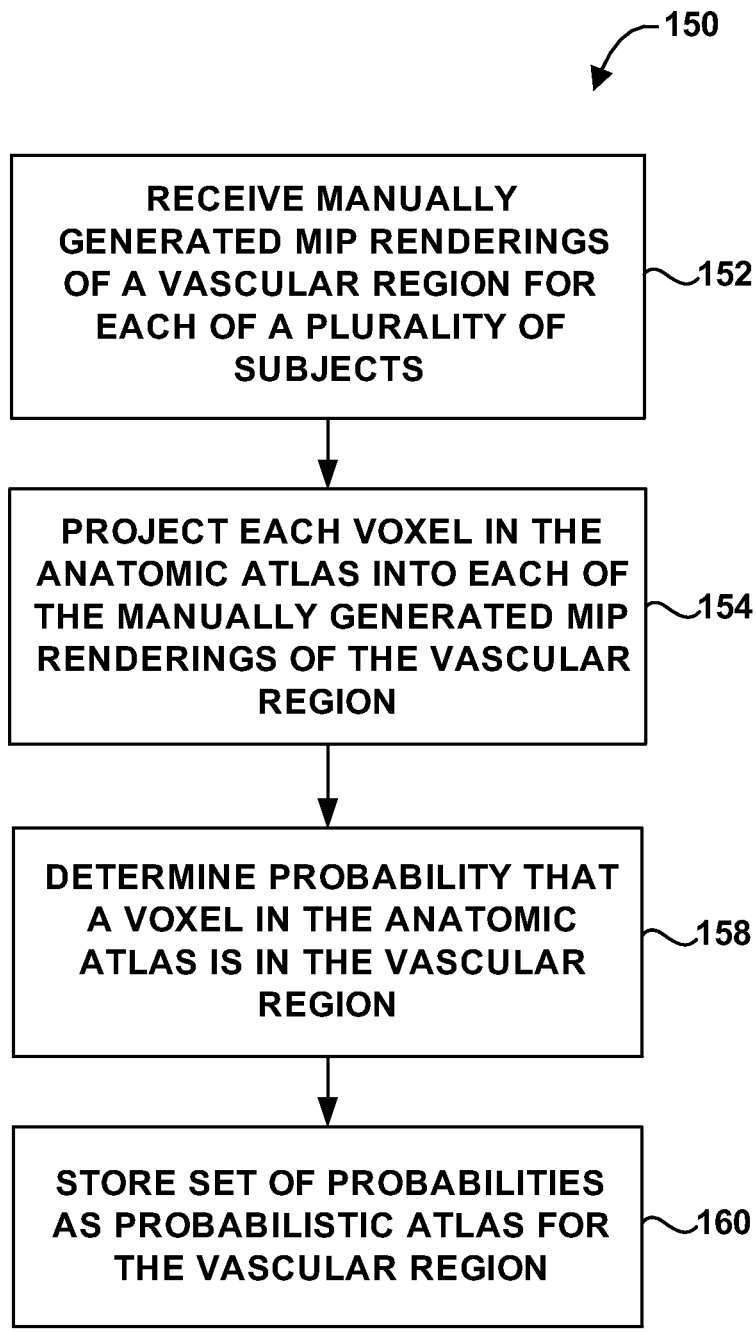
FIG. 5 is a flowchart illustrating an example process by which one or more probabilistic atlases, each corresponding to a different vascular region or regions, may be generated.

FIG. 5 is a flowchart illustrating an example process (150) by which one or more probabilistic atlases, each corresponding to a different vascular region or regions, may be generated. In this example, the one or more probabilistic atlases are generated based on the plurality of image data sets of the sample population. Each probabilistic atlas corresponds to a different vascular region to be identified and includes the probability that each voxel in an image data set is contained in the corresponding vascular region. In this example, the process (150) receives a plurality manually generated MIP renderings of the vascular regions, each corresponding to one of the plurality of subjects in the sample population (152). In this example, the sample population is the same sample population used to construct the anatomic atlas. However, the sample populations need not be the same. Each voxel in the anatomic atlas is given one or more classifications corresponding to the number of vascular regions to be identified. In this example, each voxel is given three classifications, each corresponding to the probability that the voxel is contained in one of the following three vascular regions: left carotid, right carotid and basilar vascular regions. Each voxel in the anatomic atlas is projected into each of the manually generated MIP renderings for each of the subjects corresponding to the same vascular region (154). To generate the probabilistic atlas for the left carotid region, for example, each voxel in the anatomic atlas is projected into the manually generated MIP renderings of the left carotid region for each subject in the sample population. If a voxel in any of the MIP renderings is zero, this means that the technician manually determined that that particular voxel was not a part of the vascular region at issue for that particular patient. In this way, the process reconstructs the original technician segmentation for the vascular region.

The system determines the probability that each voxel in the anatomic atlas is contained in the vascular region at issue (158). For example, for each voxel, the probability that a particular voxel is contained in a vascular region may be expressed by the total number of "hits" (that is, the number of image data sets in which that voxel was contained in the vascular region) as compared to the total number of patients in the sample population. The set of probabilities may be stored as a percentage, a ratio, on a scale from 0 (definitely not part of the vascular region) and 1 (definitely part of the vascular region), or other means of representing probability or likelihood of belonging. The set of probabilities for each voxel in the anatomic atlas is stored as the probabilistic atlas for the vascular region (160). The process (150) may be repeated to generate probabilistic atlases for each vascular region of interest. For example, the process may be repeated to generate a probabilistic atlas for each of the left carotid, right carotid, and basilar vascular regions, and/or for any other vascular regions of interest.

Figure 6:
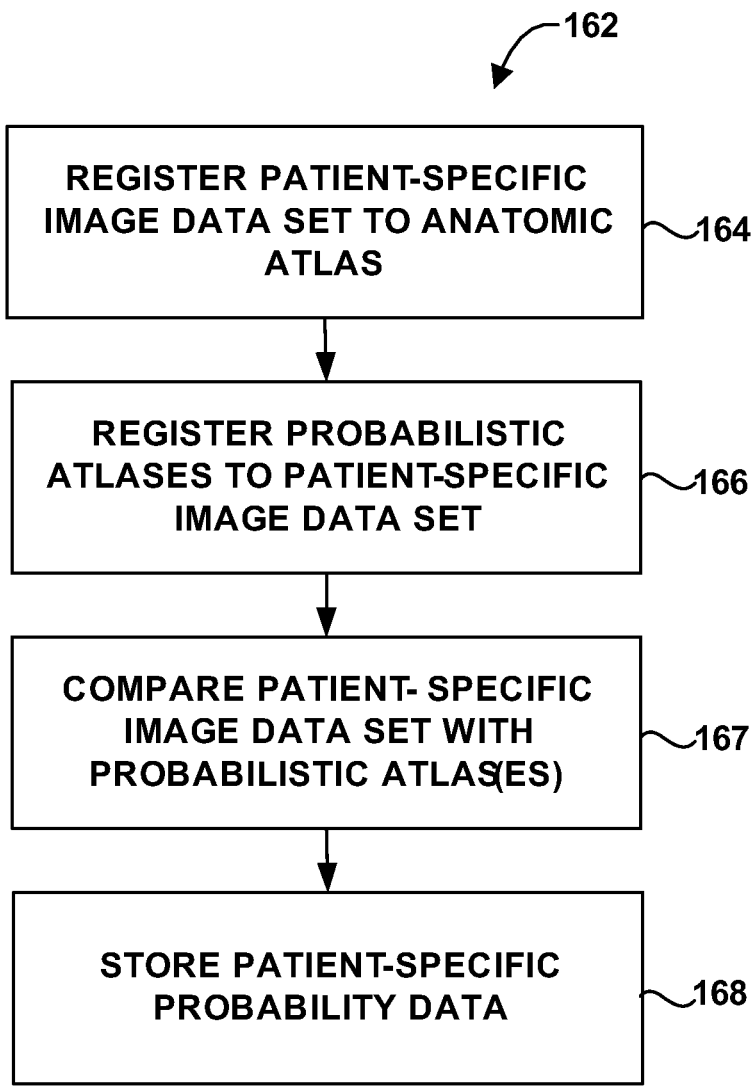
FIG. 6 is a flowchart illustrating an example process by which the system may determine the general location of the one or more vascular regions based on the anatomic atlas and the probabilistic atlases.

FIG. 6 is a flowchart illustrating an example process (162) by which the system may determine the general location of the one or more vascular regions based on the anatomic atlas and the probabilistic atlases. The system registers the patient-specific image data set to the anatomic atlas (164). The registration generates a mapping (e.g., a set of transform parameters) between the coordinate system of the patient-specific image data set and the coordinate system of the anatomic atlas. The probabilistic atlases (each of which corresponds to a different one of the vascular regions) are registered to the coordinate system of the patient-specific image data set using the transform parameters (166). The registration is accomplished using the same transform parameters used to align the patient-specific image data set with the anatomic atlas. The system then compares the patient-specific image data set with the one or more probabilistic atlases on a per voxel level (167). The resulting patient-specific probability data for each voxel in the patient-specific image data set are stored (168). In this way, each voxel in the patient-specific image data set is assigned a patient-specific probability based on a corresponding voxel in each of one or more probabilistic atlases.

Figure 7:
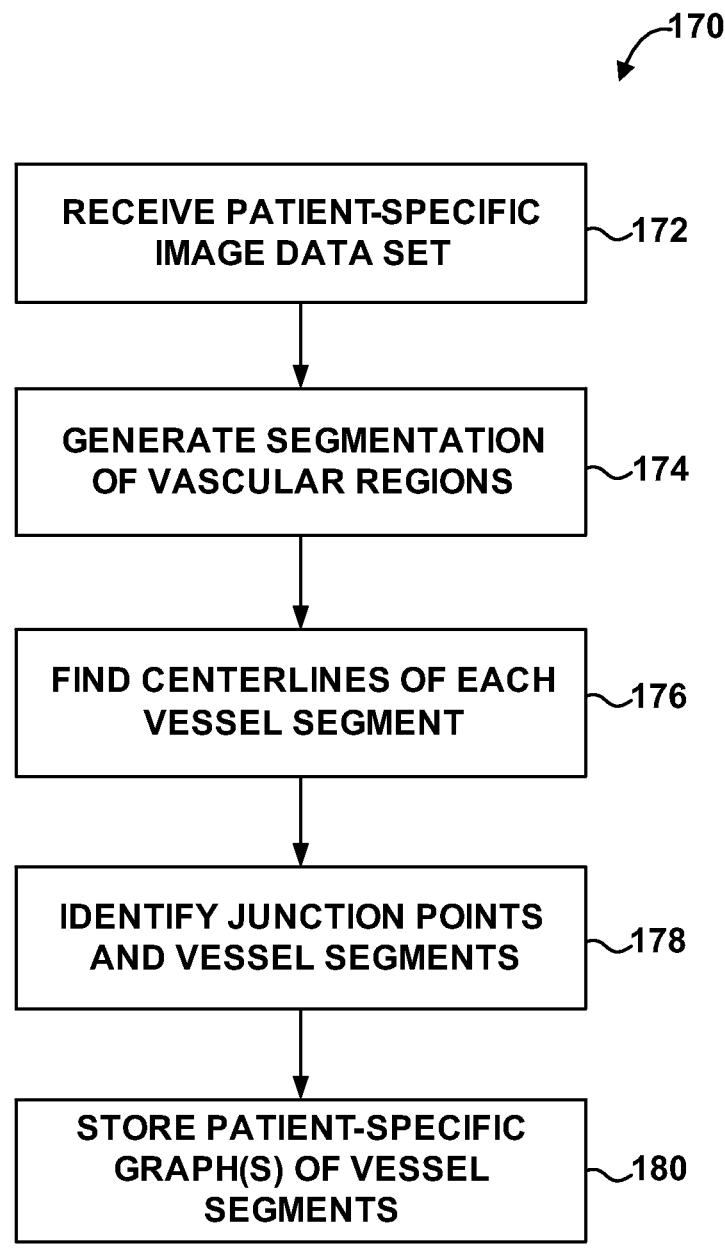
FIG. 7 is a flowchart illustrating an example process by which the system may segment and graph a patient-specific image data set.

FIG. 7 is a flowchart illustrating an example process (170) by which the system may segment and graph a patient-specific image data set. Generally, the vascular structures may be represented as a mathematical construct called a graph. A graph consists of a set of nodes N and edges E which link the nodes. Thus the graph may be considered the set of edges and nodes, G=N, E. A vessel graph is constructed from the centerline of the patient-specific segmented vasculature. The nodes of the graph correspond to vessel junctions, and the edges of the graph are the connecting vascular centerline segments. Using the graph representation, spatial interconnections between vessel segments may be analyzed.

To generate the graph, an automatic segmentation algorithm is applied (174), resulting in a binary image set containing segmented arterial vessels. One example automatic segmentation algorithm is based on a global thresholding and region growing scheme. This example segmentation method includes finding a "best" threshold and a series of seed points automatically that initiate the region growing algorithm. The segmentation algorithm generates one single or multiple separate 3D regions, each of which represents a group of connected artery vessels. The segmentation may also be performed using clustering methods, histogram-based methods, edge detection, seeded or unseeded region growing methods, level set methods, manual, automatic or semi-automatic segmentation methods, or other segmentation methods known in the art.

After the segmented image is obtained, the centerline of the vessels is determined (176). For example, for each of the 3D regions, internal holes may be mended based on the contours found in each slice. Then the centerlines of the 3D region may be calculated using a 3D thinning algorithm, such as that described in Ta-Chih Lee, et al. Building Skeleton Models via 3-D Medial Surface/Axis Thinning Algorithms, *CVGIP: Graphical Models and Image Processing.* v.56 n.6, p. 462-478, November 1994.

The system identifies the junction points (nodes) and vessel segments (edges) from the centerlines. For example, junction points (nodes) may be identified based on the number of neighbors a voxel has (178). Vessel segments are constructed of connected voxels between junction points. The graph structure is generated from the set of nodes and edges (180).

Figure 8A:
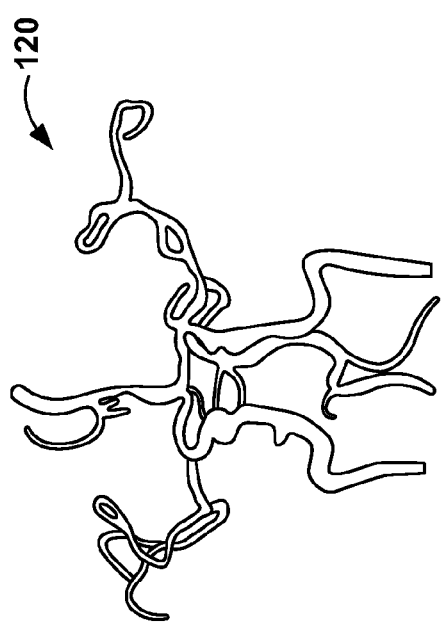
FIGS. 8A-8C show an example vessel segmentation, example centerline graphs for the vessel segmentation, and an example graph classification tree for the vessel segmentation, respectively.
Figure 8B:
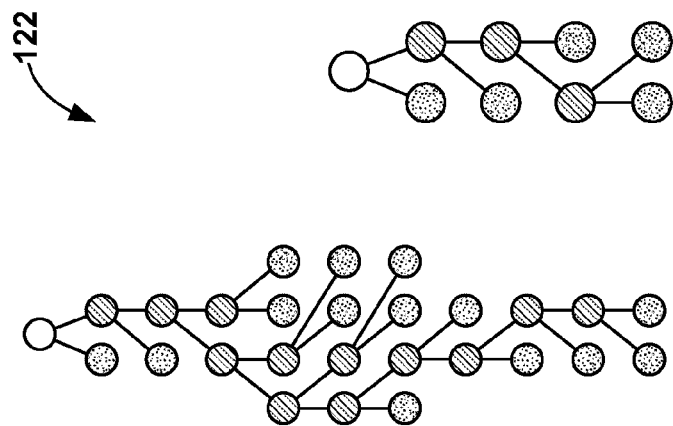

FIGS. 8A-8B show an example vessel segmentation 120, and example centerline graphs 121 for the vessel segmentation 117, and an example graph classification data structure 122 for the vessel segmentation 117, respectively.

Figure 9:
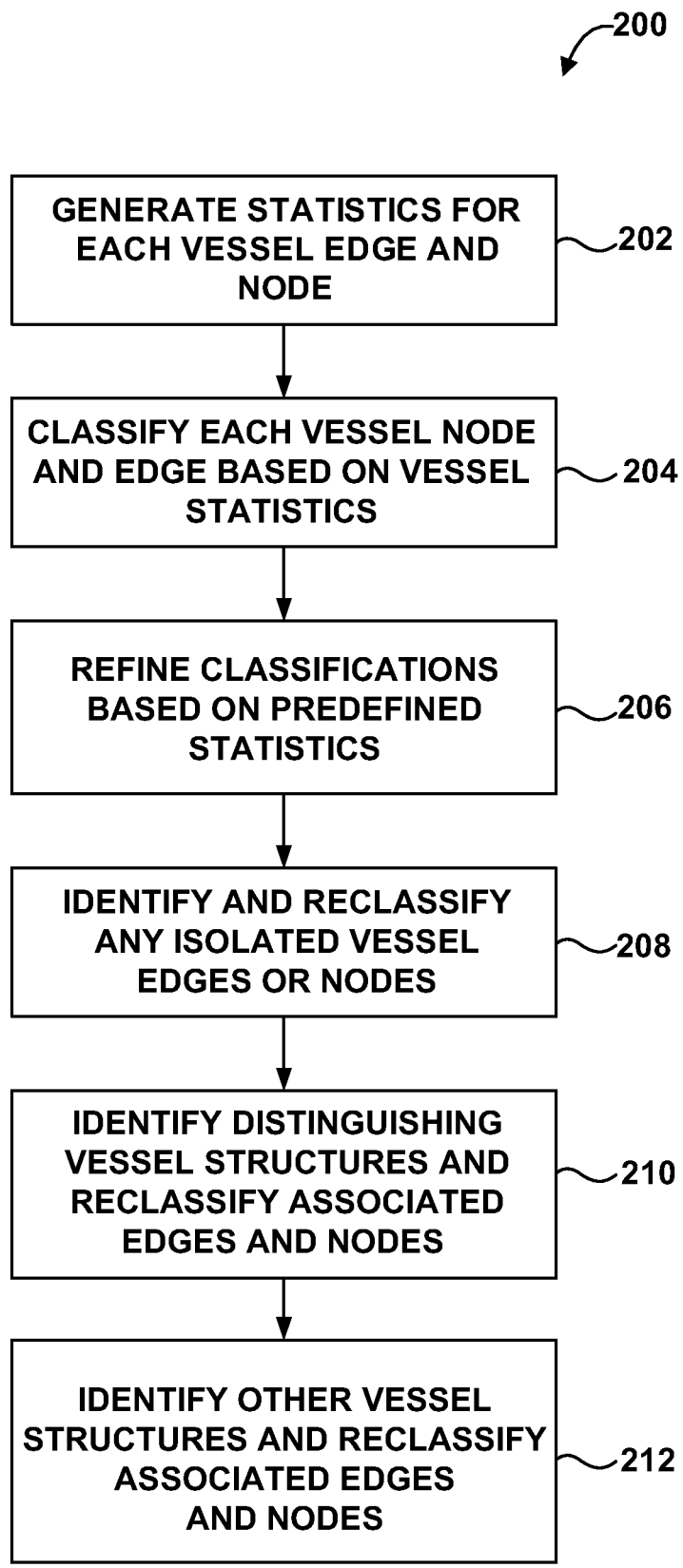
FIG. 9 shows an example process by which the system may classify each vessel segment (edge).

FIG. 9 shows an example process (200) by which the system may classify each vessel segment (edge) and node in the graph. Each edge and node may be classified based on a variety of heuristics and graph pattern searching approaches. The example process (200) illustrates a series of analysis steps to determine the vessel classification.

The system generates one or more statistics for each of the vessel edges and nodes (202). Example statistics may include: the average probabilities that this vessel edge or node, is in the left carotid, right carotid, or basilar arterial region (these averages may be obtained using the information in the probabilistic atlases and correlating it to the position of the voxels making up the centerline of the vessel edge or node as described above); a centroid of the vessel segment; a minimum radius of the vessel segment; a maximum radius of the vessel segment; an average radius of the vessel segment; an average cross sectional area of the vessel segment; a unit vector and magnitude of a line which connects the first and last voxel of the vessel segment (vessel segment direction and length); a curvature of the vessel segment; whether a node is a terminal node (nodes only); a 3-dimensional vessel location within the head; etc. In addition, the graph may be overlaid onto the one or more of the probabilistic atlases to determine the average overlap with the one or more probabilistic atlases (e.g., the basilar probabilistic atlas, the left carotid probabilistic atlas, and the right carotid probabilistic atlas). The average overlap(s) with the probabilistic atlases may also be included as a feature or features of the graph. Other examples may include the angle between two vessels at a junction and/or the localized probability within a subsegment of the vessel. Although certain example statistics have been listed, it shall be understood that the listed statistics are examples only, that other appropriate statistics may also be used, and that the disclosure is not limited in this respect.

The vessel nodes and edges are classified based on the vessel statistics (204). Each vessel node and edge is classified according to the region or regions to which it most likely belongs. In some examples, there may be overlap between the volume of space covered by the probabilistic atlases for the vessel regions. This means that analyzing the statistical probability that a particular vessel belongs to a particular region may be imprecise. For example, when the vascular regions to be identified are the basilar, right carotid and left carotid vascular regions, there are eight possible combinations and therefore eight possible classifications. This is because each vessel edge or node could be entirely in the basilar, right carotid, or left carotid region, in any combination of the three regions, or in none of the regions. For example, there may be an indication that there is a 65% probability that a given vessel segment is in the right carotid region, and at the same time a 65% probability that it's in the left carotid region. In this example, each vessel segment is given one of eight possible classifications:
1. Right Carotid
2. Left Carotid
3. Basilar
4. Right and Left Carotid
5. Right Carotid and Basilar
6. Left Carotid and Basilar
7. Right Carotid, Left Carotid, and Basilar
8. Undefined (i.e. all three probabilities are zero)

The classification of the nodes and/or edges may be accomplished by analyzing the ratios of the 3 probabilities and classifying them based on the ranges. For example, the following ratios may be determined: R/L=Right Carotid/Left Carotid probabilities; R/B=Right Carotid/Basilar probabilities; and L/B=Left Carotid/Basilar probabilities. The ranges for each of these ratios may be determined via experimentation on a sufficient sample size. The region classification may then be assigned, for example, as follows: If $R/L > 3/2$ and $R/B > 3/2$ then R is clearly dominant so it may be labeled as Right Carotid. Note that this assumes the base probabilities are not too small (i.e. they should be at least 1). Other nodes and/or edges could be classified in a similar manner. Sometimes the ratios may be such that a node or edge could be classified as being a part of two or even three regions. For example, if $2/3 < R/L < 3/2$ and $2/3 < R/B < 3/2$ and $2/3 < L/B < 3/2$ then that part may be classified as being in all three regions.

The classifications may be refined based on certain predefined vessel statistics (206). In this example, the system attempts to find a major section of either left or right carotid that may have been mistakenly classified as basilar in (204). For example, the vessel's length, average radius, and centroid may be analyzed. If the vessel is "long" (relative to typical basilar vessel segments), has a larger radius, and/or is located below the normal center of the head, then it is likely one of the major sections of a carotid. If it was classified otherwise (e.g., as possibly being basilar), the classification is refined. The predefined vessel statistics to be analyzed may depend at least in part upon the particular vessel region(s) to be identified.

The system identifies and reclassifies any isolated vessel edges or nodes (208). An isolated edge (or node) is one in which all of the nodes and edges surrounding the isolated edge (or node) have the same classification, and the isolated node or edge has a different classification. An isolated node or edge may be reclassified to match the surrounding nodes and edges. Thus, for example, if all of a particular edge's (or a node's) neighbors are classified basilar, then it is very unlikely that the edge (or node) belongs to the left or right carotid. That edge (or node) is an isolated edge (or node), and the isolated edge (or node) may be reclassified as basilar.

The system analyzes the graph to identify one or more distinguishing vessel structures that may allow for further refining of the classifications (210). For example, the system may analyze the vessel graph to identify a structure in the bottom part of the basilar region that looks like an upside down 'Y' on an image. This may help to refine which vessels belong to the basilar vascular region. In addition, once the vessels of the basilar Y structure are identified, then the bottom segments of the left and right carotids may also be identified. This process may be broken down into a series of sub-steps as follows. Note that this example is specific to identifying the basilar Y structure, and that a similar or other relevant process may be used to identify other distinguishing vessel structures depending upon the vessel regions to be identified.

"Pruning" Pruning removes minor or relatively smaller vessels from the main vessel structure. The vessel cross-sectional size is compared to a pruning limit. The pruning limit is determined based on known sizes of the vessels in the basilar Y structure. If the vessel is smaller than the pruning limit, the vessel is removed from consideration. If the smaller vessels are not pruned, the routine may wrongly interpret the structure it is analyzing. Pruning is done along the way during the steps below.

Starting with all terminal nodes (vessel endpoints not connected to another vessel) that are within a certain distance of the bottom of the image, traverse the vessel edges and nodes looking for features that identify the basilar Y structure. Save all such candidate structures for later evaluation. For example:
   a. If the starting vessel is smaller than the pruning limit, this is not a candidate.
   b. Only consider edges that are within at least one of the probabilistic atlases.
   c. Starting with the current edge, find the other two edges that meet at the node at the far end of this edge (the far node). If there are no other edges (i.e. the node is terminal) this edge is not a candidate.

d. If both the edges beyond the far node are not "prunable", then the far node is a candidate for the "main junction" of the basilar Y structure.

e. Both vessels leading out from the main junction candidate are recursively followed, pruning along the way, until either a terminal node is reached, or two qualified (above the pruning limit) vessel leave a node. This is the end of one of the legs/arms of the basilar Y structure candidate. Mark the node as a final node.

f. Save all the vessels and nodes that make up this basilar Y structure candidate and repeat with the next edge starting at step c.

Determine which one, if any, of the basilar Y candidates is the actual basilar Y structure. The following qualification features may be used:

a. Main junction node has a probability of being basilar greater than zero.

b. The main junction's vertical location is below the junction maximum vertical limit.

c. The number of final nodes, which includes the starting node, is three.

d. Find the two nodes with the smallest z values, and average their y values. The assumption is that the bottom two terminal nodes of the basilar Y structure will be closest to the back of the brain, which would result in them having relatively lower y values.

If all the above conditions are met, the system reclassifies, if needed, the vessel edges and nodes that are part of the Y structure as basilar. The system also classifies any vessels which were pruned from the basilar Y structure nodes and edges as being basilar since they are part of the same structure.

The system analyzes the graph to identify one or more other vessel structures that may allow for further refining of the classifications (212). For example, if the location of the basilar Y structure has been identified, the system may attempt to identify the main trunk of the left carotid and/or the main trunk of the right carotid. This may be somewhat simplified once the basilar Y structure has been identified. The main trunk of the left carotid and right carotid may be identified as large vessels, in the lower part of the brain, to the right or left of the basilar Y structure. These are then reclassified appropriately as needed. Note that this example is specific to identifying the left and right carotids based on an identification of the basilar Y structure, and that a similar process may be used to identify other vessel structures depending upon the vessel regions to be identified.

Figure 8C:
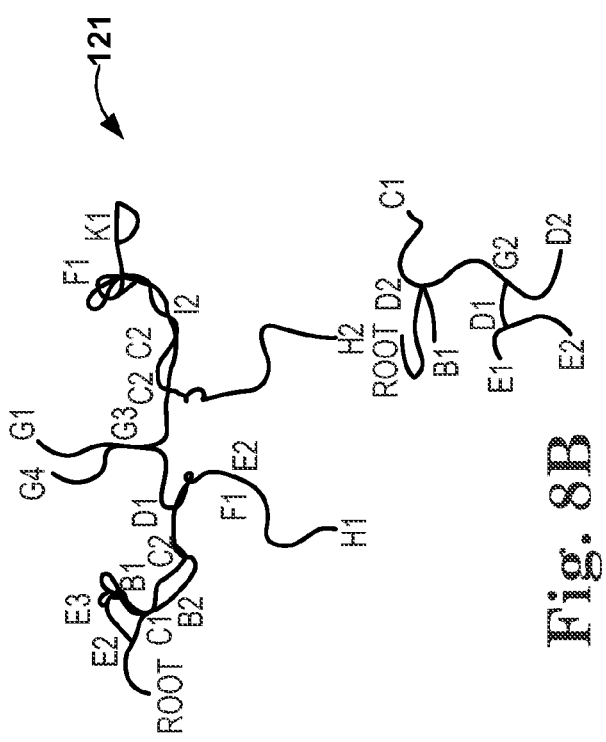

FIG. 8C shows an example graph classification data structure for the vessel segmentation of FIG. 8A.

Figure 10:
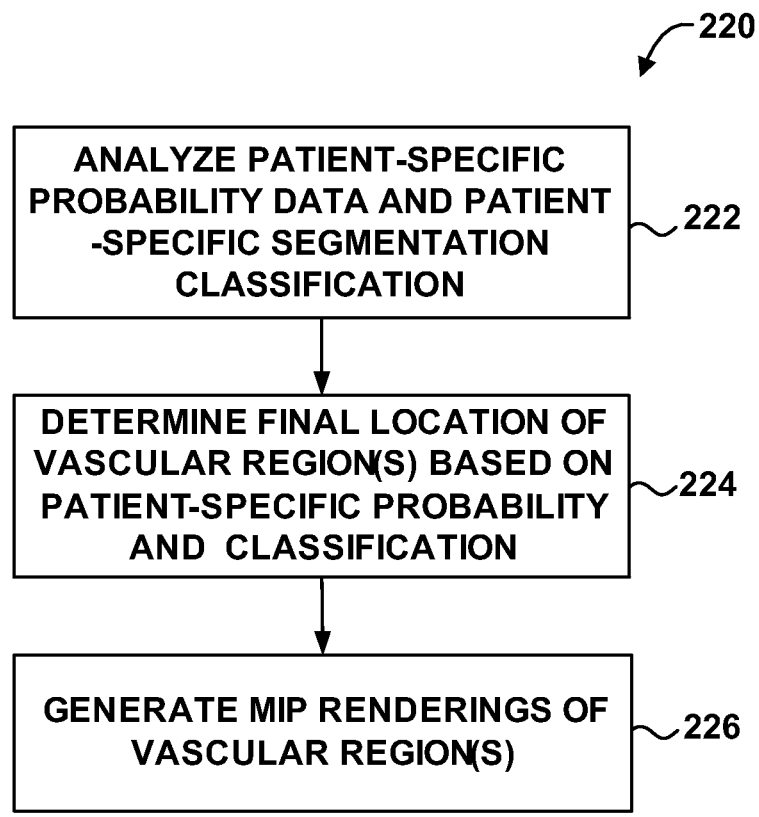
FIG. 10 is a flowchart illustrating an example process by which the system determines the location of the one or more vascular regions in the patient-specific image data set, and may also generate a MIP rendering of the one or more vascular regions.

FIG. 10 is a flowchart illustrating an example process (220) by which the system automatically determines the location of the one or more vascular regions in the patient-specific image data set, and may also generate a MIP rendering of the one or more vascular regions. The determination is based on an analysis of the patient-specific probability data (determined, for example, as shown in FIG. 6) and the patient-specific segmentation classifications (determined, for example, as shown in FIG. 6) (222). The patient-specific probability data can be used to further refine the segmentation classifications to arrive at a final classification (224). For example, the patient-specific probability data may be combined with the patient-specific classifications to add vessels that were missed by one or more of the probabilistic atlases and/or to remove vessels that should not have been included in each vascular region. Since each edge or node is given one of 7 different classifications, this information may be used to specifically add or remove regions from the probabilistic atlases. For example, if for a particular case the basilar region of the basilar probabilistic atlas does not cover the patient-specific basilar vessels completely, the segmented vessels that are classified as basilar together with a 3D neighborhood around the vessel edge may be added to the basilar region for the patient-specific image data set.

For example, if the patient-specific probability for a voxel in the patient-specific image data set indicates that the voxel belongs to a particular one of the vascular regions and the classification also indicates that the voxel belongs to that vascular region, the system may determine that the voxel belongs to that vascular region. If the patient-specific probability for a voxel in the patient-specific image data set indicates that the voxel does not belong to the particular vascular region, but the classification indicates that the voxel does belong to that vascular region, the system may determine that the voxel belongs to that vascular region. If the patient-specific probability for a voxel in the patient-specific image data set indicates that the voxel belongs to a particular vascular region, but the classification indicates that the voxel does not belong to that vascular region, the system may determine that the voxel does not belong to that vascular region. If the patient-specific probability for a voxel in the patient-specific image data set indicates that the voxel does not belong to a particular vascular region and the classification also indicates that the voxel does not belong to that vascular region, the system may determine that the voxel does not belong to that vascular region.

In some examples, MIP renderings of the one or more vascular regions may be generated from the final classifications of the segmented image (226).

In one example, for each region, the process in Algorithm 1 may be applied to produce the final segmentation. It shall be understood, however, that Algorithm 1 is only one example of how the process may be implemented, and that the disclosure is not limited in this respect.

Algorithm 1: Region separation:

Require: TOF
Require: $T_{A \to P}$
Require: $P_L, P_R, P_B$
   for all Region ∈ L, R, B do
      {Transform and threshold}
      $P'_{Region} = T_{A \to P} \circ P_{Region}$
      $S_{Region} = P'_{Region} > T$
      {Remove or add regions}
      for all V ∈ N do
         {d(V) generates a region about the vessel V}
         if V labeled as Region then
            $S_{Region} += d(V)$
         else
            $S_{Region} -= d(V)$
         end if
      end for
      {Generate MIP rendering}
      $MIP(S_{region})$
   end for FIGS. 11A-11C show examples of automatically generated MIP renderings of the left carotid vascular region 124, right carotid vascular region 126, and basilar vascular region 128.

FIGS. 12A-12C show examples of manually (technician) generated MIP renderings of the left carotid vascular region 144, right carotid vascular region 146, and basilar vascular region 148.

Figure 13:
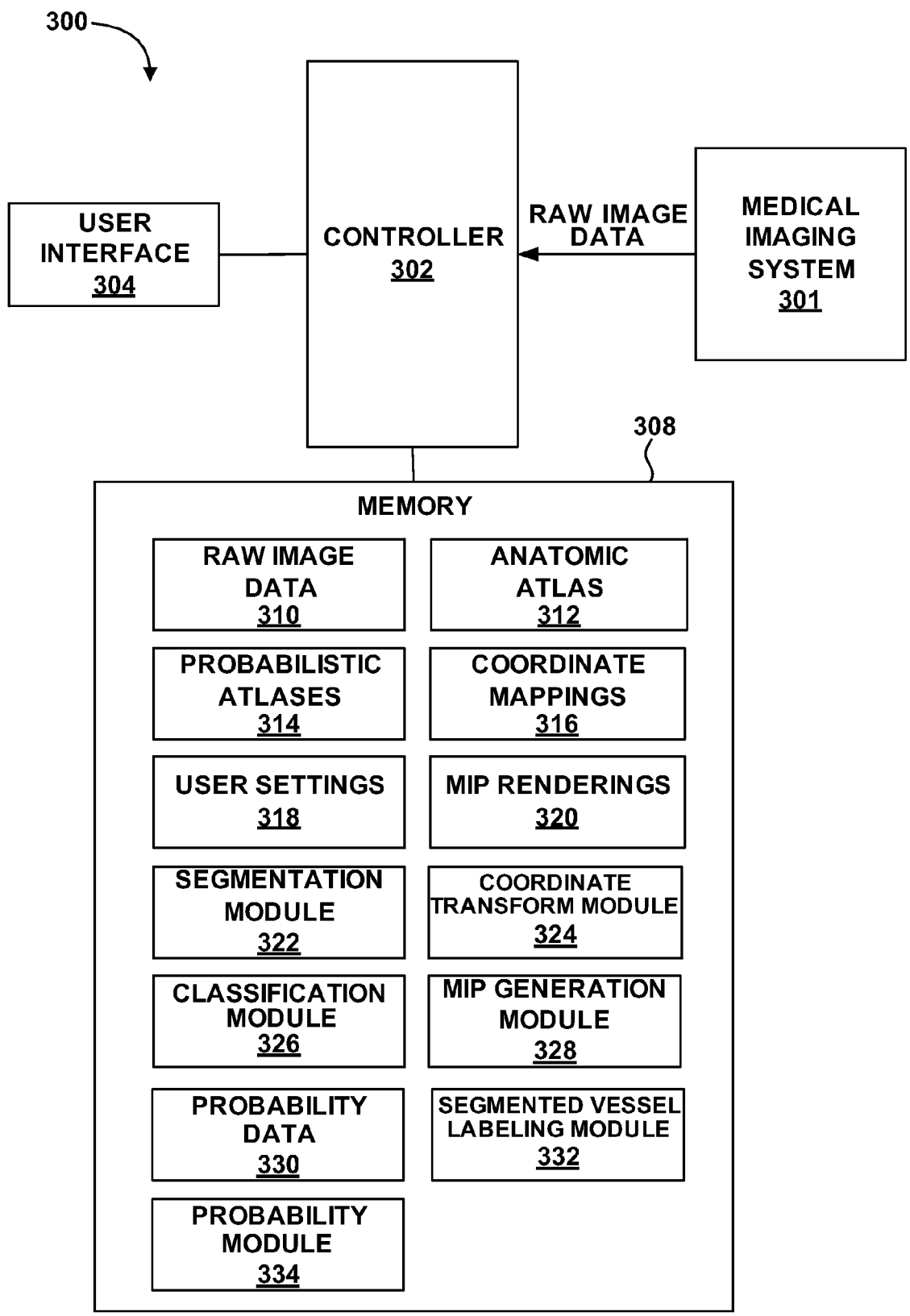
FIG. 13 is a block diagram illustrating an example automatic vascular region separation system.

FIG. 13 is a block diagram illustrating an example automatic vascular region separation system 300. System 300 includes a controller 302 that receives raw image data from one or more medical imaging system(s) 301, such a magnetic resonance imaging (MRI) system, a computed tomography (CT) system, etc. A user interface 304 may include a display, keyboard or key pad, mouse, touch screen or other means of displaying data or images, receiving input from or otherwise interfacing with a user. The various components of system 300 may communicate via one or more of a hard-wired connection, a wireless connection, or via a network such as a local area network or wide area network. In addition, one or more components of system 300 may communicate via the internet, satellite, telephone, cellular phone network or via other means of remote electronic communication.

One or more data storage devices, represented generally by memory 308, store information, such as software modules executed by the controller and data used or generated by the controller during such execution. Memory 308 may be implemented in any of several different ways. For example, memory 308 may include one or more different types of memory, e.g., random access memory (RAM), electrically erasable programmable read-only memory (EEPROM), FLASH memory, etc. Some portions of memory 308 may be collocated on-chip with controller 302 (e.g., in the case of microcontroller) or may be on a separate component (e.g., in the case of a FLASH memory or EEPROM).

Regardless of the implementation, memory 308 may store a variety of data and/or functional software modules. For example, memory 308 may store raw image data 310; the anatomic atlas 312; the probabilistic atlases for each vascular region 314; coordinate mappings 316; user settings 318; the automatically generated MIP renderings 320; patient-specific probability data 330, and/or any other data used by or generated by controller 302 during the course of automatically performing vascular region separation.

Memory 308 may also store a segmentation module 322 that generates the segmented image (as shown in FIG. 7, for example); a coordinate transform module 324 that determines coordinate system (transform) mappings and transforms between coordinate systems using the coordinate system mappings 316; a classification module 326 that classifies each node and edge in the segmented image (as shown in FIG. 9, for example); a probability module 334 that determines the probability for each voxel in a patient-specific image data set that the voxel belongs to one or more vascular regions of interest (as shown in FIG. 6, for example); a vessel location analysis module 332 that determines the location of the one or more vessel regions in a patient-specific image data set based on the patient-specific probability data and the patient-specific classifications (as shown in FIG. 10, for example); and a MIP generation module 328 that automatically generates MIP renderings from the segmented images.

User settings 318 allow the user to define or customize a variety of user adjustable settings for viewing and interacting with the various components of system 300. For example, the user may select which image(s) (e.g., raw images, segmented images, probabilistic images, manually generated MIP images, automatically generated MIP images, etc.) view at various points during the automatic vascular separation process. The user may choose to view the data through maximum intensity projection (MIP) or volume rendering to aid the user's perception in visualizing the relative 3D positions of the identified vascular regions within the intracranial space. The user may also select how the data is to be viewed. For example, the user may be presented with a series of bookmarks, each associated with a different patient and/or a different vascular region, that the user may then scroll through and review.

Figure 14A:
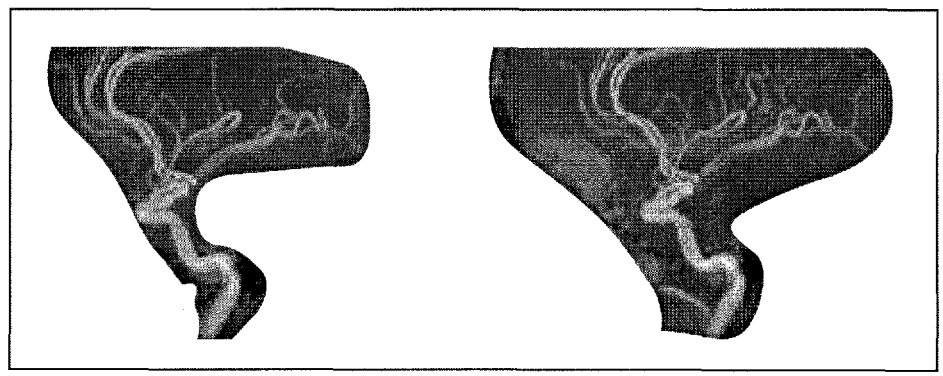
FIGS. 14A-14C show additional examples of automatic (left side) and technician (right side) generated MIP renderings of the left carotid, right carotid, and basilar vascular regions, respectively.
Figure 14B:
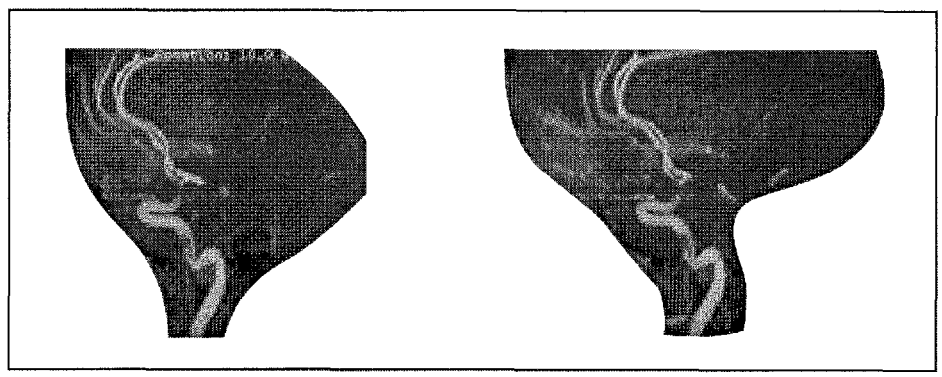
Figure 14C:
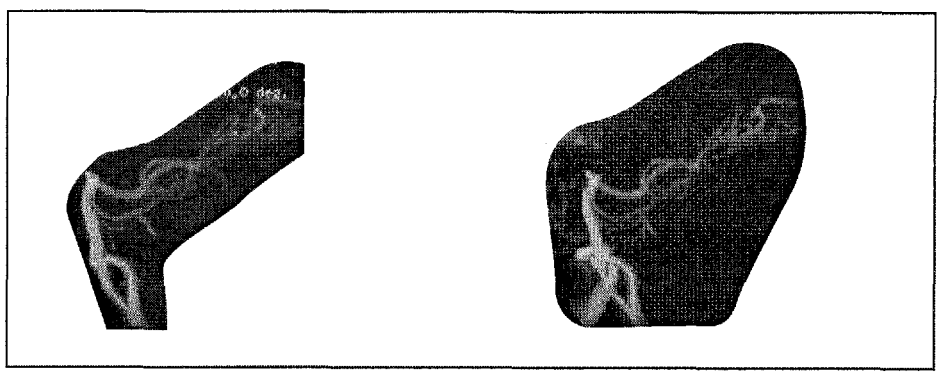

FIGS. 14A-14C show additional examples of automatic (left side) and technician (right side) generated MIP renderings of the left carotid, right carotid, and basilar vascular regions, respectively.

One or more of the techniques described herein may be partially or wholly executed in software. For example, a computer-readable medium may store or otherwise comprise computer-readable instructions, i.e., program code that can be executed by a computer or processor to carry out one of more of the techniques described above.

As another example, the disclosure may encompass one or more computer-readable media comprising instructions that cause a processor to carry out the methods described above. A "computer-readable medium" includes but is not limited to read-only memory (ROM), random access memory (RAM), non-volatile random access memory (NVRAM), electrically erasable programmable read-only memory (EEPROM), flash memory, a magnetic hard drive, a magnetic disk or a magnetic tape, a optical disk or magneto-optic disk, CD, CD-ROM, DVD, a holographic medium, or the like. The instructions may be implemented as one or more software modules, which may be executed by themselves or in combination with other software.

The instructions and the media are not necessarily associated with any particular computer or other apparatus, but may be carried out by various general-purpose or specialized machines. The instructions may be distributed among two or more media and may be executed by two or more machines. The machines may be coupled to one another directly, or may be coupled through a network, such as a local access network (LAN), or a global network such as the Internet. The connections may be wired or wireless.

As another example, the techniques described herein may be embodied as one or more devices that include logic circuitry to carry out the functions or methods as described herein. The logic circuitry may include a processor that may be programmable for a general purpose or may be dedicated, such as microcontroller, a microprocessor, a Digital Signal Processor (DSP), an Application Specific Integrated Circuit (ASIC), a field programmable gate array (FPGA), and the like.

Various examples have been described. These and other examples are within the scope of the following claims.

The invention claimed is:

1. A method comprising:
   for each voxel in a patient-specific image data set and for each of one or more vascular regions of interest, determining, by a computing system, a probability that the voxel belongs to the vascular region of interest;
   segmenting patient-specific vasculature in the patient-specific image data set to generate a set of nodes and edges representative of the patient-specific vasculature;
   for each node and edge, assigning, by the computing system, a classification based on one or more vessel statistics associated with each node and edge, the classification indicative of which of the one or more vascular regions of interest the associated voxel belongs;
   determining, by the computing system, to which of the one or more vascular regions of interest each voxel in the patient-specific image data set belongs based on the probability and the classification for each voxel; and
   generating, by the computing system and for display, a rendering of the one or more patient-specific vascular regions of interest based on the determination.

2. The method of claim 1 wherein determining to which of the one or more vascular regions of interest each voxel belongs comprises determining whether each voxel in the patient-specific image data set belongs to a left carotid vascular region, a right carotid vascular region or a basilar vascular region.

3. The method of claim 1 wherein the rendering of the vascular region of interest is a maximum intensity projection (MIP) rendering.

4. The method of claim 1 wherein determining a probability for each voxel comprises assigning each voxel in the patient-specific image data set one or more patient-specific probabilities based on a corresponding voxel in each of one or more probabilistic atlases, each probabilistic atlas corresponding to a different one of the vascular regions.

5. The method of claim 1 wherein determining to which of the one or more vascular regions of interest each voxel belongs comprises:
- if the patient-specific probability for a voxel in the patient-specific image data set indicates that the voxel belongs to a first one of the vascular regions and the classification indicates that the voxel belongs to the first vascular region, determining that the voxel belongs to the first vascular region;
- if the patient-specific probability for a voxel in the patient-specific image data set indicates that the voxel does not belong to the first one vascular region and the classification indicates that the voxel belongs to the first vascular region, determining that the voxel belongs to the first vascular region;
- if the patient-specific probability for a voxel in the patient-specific image data set indicates that the voxel belongs to the first vascular region and the classification indicates that the voxel does not belong to the first vascular region, determining that the voxel does not belong to the first vascular region; and
- if the patient-specific probability for a voxel in the patient-specific image data set indicates that the voxel does not belong to the first vascular region and the classification indicates that the voxel does not belong to the first vascular region, determining that the voxel does not belong to the first vascular region.

6. The method of claim 1 wherein classifying each voxel based on one or more statistics comprises classifying each voxel based on one or more of the average probabilities that the voxel is in the left carotid, right carotid, or basilar arterial region; a centroid of the vessel segment; a minimum radius of the vessel segment; a maximum radius of the vessel segment; an average radius of the vessel segment; an average cross sectional area of the vessel segment; a direction of the vessel segment; a length of the vessel segment; a curvature of the vessel segment; whether a node is a terminal node; and a 3-dimensional location within the patient's head of the vessel segment.

7. A system comprising:
- a controller that receives a patient-specific image data set;
- a probability module, executed by the controller, that determines a probability for each voxel in a patient-specific image data set that the voxel belongs to one or more vascular regions of interest;
- a segmentation module, executed by the controller, that segments patient-specific vasculature in the patient-specific image data set to generate a set of nodes and edges representative of the patient-specific vasculature;
- a classification module, executed by the controller, that assigns a classification to each node and edge based on one or more vessel statistics associated with each node and edge, the classification indicative of which of the one or more vascular regions of interest the associated voxel belongs; and
- a vessel location analysis module, executed by the controller, that determines to which of the one or more vascular regions of interest each voxel in the patient-specific image data set belongs based on the probability and the classification for each voxel.

8. The system of claim 7 wherein the vascular region of interest comprises one or more of a left carotid vascular region, a right carotid vascular region, or a basilar vascular region.

9. The system of claim 7 further including a manual intensity projection (MIP) module, executed by the controller, that automatically generates a MIP rendering of the vascular region of interest based on the determination.

10. The system of claim 7 further including a user interface that displays the MIP rendering.

11. The system of claim 7 wherein the probability module assigns each voxel in the patient-specific image data set a patient-specific probability based on a corresponding voxel in each of one or more probabilistic atlases, each probabilistic atlas corresponding to a different one of the vascular regions.

* * * * *